(12) United States Patent
Morris

(10) Patent No.: US 6,857,430 B2
(45) Date of Patent: Feb. 22, 2005

(54) RESTRAINING HARNESS

(76) Inventor: Dane Michael Morris, 1698 Shakespeare St., Sebastian, FL (US) 32958

( * ) Notice: Subject to any disclaimer, the term of this patent is extended or adjusted under 35 U.S.C. 154(b) by 113 days.

(21) Appl. No.: 10/235,818

(22) Filed: Sep. 6, 2002

(65) Prior Publication Data

US 2004/0045559 A1 Mar. 11, 2004

(51) Int. Cl.$^7$ .............................................. A61B 19/00
(52) U.S. Cl. ...................... 128/869; 128/875; 128/876
(58) Field of Search ................................ 128/846, 869, 128/874, 875, 876, 870, 873; 297/256.16, 464, 466, 467, 468, 465, 469, 479, 483; 244/122 R, 122 AG, 122 B

(56) References Cited

U.S. PATENT DOCUMENTS

| | | | | | |
|---|---|---|---|---|---|
| 1,310,958 | A | * | 7/1919 | O'Connor | 297/484 |
| 2,979,028 | A | * | 4/1961 | Zakely | 182/3 |
| 3,325,213 | A | * | 6/1967 | Levy | 297/467 |
| 3,380,776 | A | * | 4/1968 | Dillender | 297/484 |
| 3,701,395 | A | * | 10/1972 | Theobald | 128/873 |
| 3,819,197 | A | * | 6/1974 | Shakespear | 297/478 |
| 3,905,615 | A | * | 9/1975 | Schulman | 280/730.1 |
| 3,954,280 | A | * | 5/1976 | Roberts et al. | 280/801.2 |
| 4,004,583 | A | | 1/1977 | Johnson | |
| 4,050,737 | A | * | 9/1977 | Jordan | 297/465 |
| 4,231,616 | A | * | 11/1980 | Painter | 297/481 |
| 4,302,049 | A | * | 11/1981 | Simpson | 297/484 |
| 4,396,228 | A | * | 8/1983 | Go | 297/484 |
| 4,402,548 | A | * | 9/1983 | Mason | 297/464 |
| 4,487,383 | A | * | 12/1984 | Mazelsky | 244/122 R |
| 4,923,147 | A | * | 5/1990 | Adams et al. | 244/122 AG |
| 4,995,672 | A | | 2/1991 | Corcoran | |
| 5,031,639 | A | * | 7/1991 | Wolfer | 128/874 |
| 5,211,186 | A | | 5/1993 | Shoemaker et al. | |
| 5,496,092 | A | * | 3/1996 | Williams et al. | 297/250.1 |
| 5,503,461 | A | | 4/1996 | Schreier | |
| 5,540,403 | A | * | 7/1996 | Standley | 244/122 B |
| 5,755,235 | A | | 5/1998 | Magiawala et al. | |
| 5,992,884 | A | | 11/1999 | Gillespie et al. | |
| 6,364,417 | B1 | * | 4/2002 | Silverman | 297/464 |
| 6,367,882 | B1 | * | 4/2002 | Van Druff et al. | 297/484 |
| 6,499,149 | B2 | * | 12/2002 | Ashline | 2/468 |

* cited by examiner

Primary Examiner—Aaron J. Lewis
(74) Attorney, Agent, or Firm—Stephen R. Greiner

(57) ABSTRACT

A restraining harness for use in land vehicles including a torso binder and an anchor assembly for securing the torso binder adjacent a seat so as to restrain a handcuffed prisoner. A number of releasable fasteners associated with the torso binder and the anchor assembly permit the torso binder to be rapidly attached and detached from the torso binder.

9 Claims, 4 Drawing Sheets

RESTRAINING HARNESS

FIELD OF THE INVENTION

The present invention relates generally to chairs and seats, and, more particularly, to occupant restraints used therewith.

BACKGROUND OF THE INVENTION

According to a recent Justice Department report, the number of people held in U.S. prisons, jails and other correctional facilities now exceeds two million. On any given day, thousands of prisoners are being transported to and from these facilities. For short trips, automobiles are normally used as a means for transportation.

While being transported in automobiles, prisoners are usually restrained by handcuffs binding their wrists together for the safety of all vehicle occupants. Because handcuffs only restrict the arms of a wearer, handcuffed prisoners sometimes move about the interior of automobiles and, as a result, cause injury to: themselves, the automobiles they are riding in, and the people charged with maintaining their custody. These injuries are, more often than not, the result of deliberate acts to escape.

Experience has shown that a determined prisoner in handcuffs can open the factory-installed seat belts in an automobile thus permitting him virtually unimpeded movement. To address this problem, special bindings and straight jackets have been proposed for limiting prisoners' movements in automobiles. Unfortunately, these products have proven to be difficult to use and unsafe in emergencies when fast evacuation from a vehicle is required. For these reasons, law enforcement agencies have not adopted such products for standard use. A need, therefore, exists for a product that permits control over the movements of a prisoner while in a vehicle to be maintained at all times, yet is safe and easy to use.

SUMMARY OF THE INVENTION

In light of the problems associated with the known products for preventing prisoner movement in a vehicle, it is a principal object of the invention to provide a restraining harness that fixes a handcuffed prisoner in a predetermined location in a vehicle, usually in a spot where he may be further restrained by the factory-installed seat belts in the vehicle for maximum safety. The restraining harness further prevents the handcuffed prisoner from disengaging the factory-installed seat belts normally binding him in a seated position. In fact, a handcuffed prisoner is effectively prevented by the restraining harness from moving his entire upper body more than a few inches in any one direction. Thus, use of the restraining harness virtually eliminates the possibility of a prisoner escaping without the aid of others.

It is another object of the invention to provide a restraining harness of the type described that can be installed in virtually any vehicle with minimal effort using conventional tools. One embodiment of the restraining harness relies on the presence of a conventional child safety seat mount in a vehicle for securement. Use of the restraining harness is intuitive and can be accomplished with minimal training.

It is a further object of the invention to provide a restraining harness of the type described that does not interfere with the operation of the factory-installed seat belts in a vehicle but, rather, supplements those seat belts by preventing a handcuffed prisoner from disengaging them. The restraining harness can be used, by way of example, in vehicles such as: automobiles, trucks, SUVs, vans, airplanes and boats.

Still another object of the invention is to provide a fully adjustable restraining harness that can be easily engaged with, and quickly released from, a handcuffed prisoner of virtually any size. Either task can be accomplished by authorized personnel in a matter of seconds.

It is an object of the invention to provide improved elements and arrangements thereof in a restraining harness for the purposes described which is lightweight in construction, inexpensive to manufacture, and dependable in use.

Briefly, the restraining harness in accordance with this invention achieves the intended objects by featuring a torso binder having a pair of shoulder straps secured to a crotch strap so as to project upwardly and outwardly therefrom. Each of the shoulder and crotch straps has a first releasable fastener portion secured thereto. An anchor assembly selectively secures the torso binder adjacent to a vehicle seat. The anchor assembly has a number of second releasable fastener portions, each adapted for selective mated engagement with a respective one of the first releasable fastener portions.

The foregoing and other objects, features and advantages of the present invention will become readily apparent upon further review of the following detailed description of the preferred embodiments as illustrated in the accompanying drawings.

BRIEF DESCRIPTION OF THE DRAWINGS

The present invention may be more readily described with reference to the accompanying drawings, in which.

Similar reference characters denote corresponding features consistently throughout the accompanying drawings.

DETAILED DESCRIPTION OF THE PREFERRED EMBODIMENTS

Figure 1:
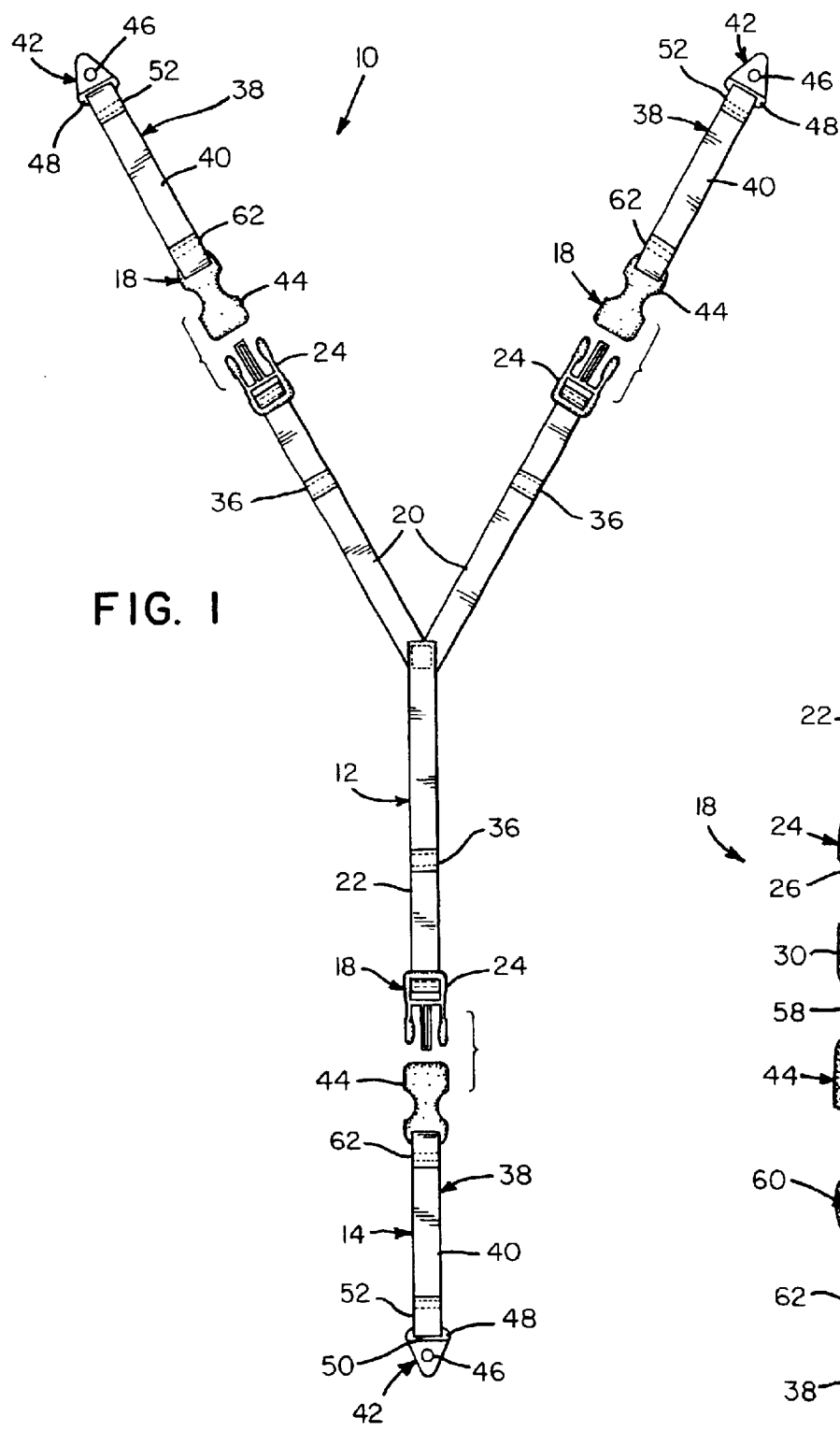
FIG. 1 is a front elevational view of a restraining harness in accordance with the present invention.
Figure 2:
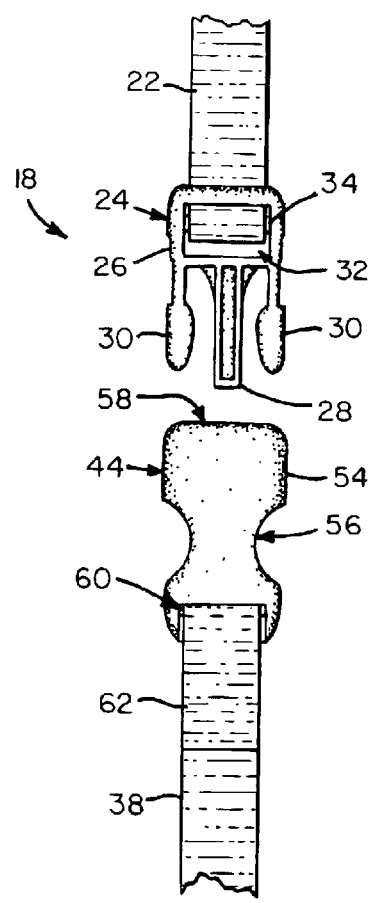
FIG. 2 is a front elevational view of a releasable fastener used in the restraining harness of FIG. 1.
Figure 3:
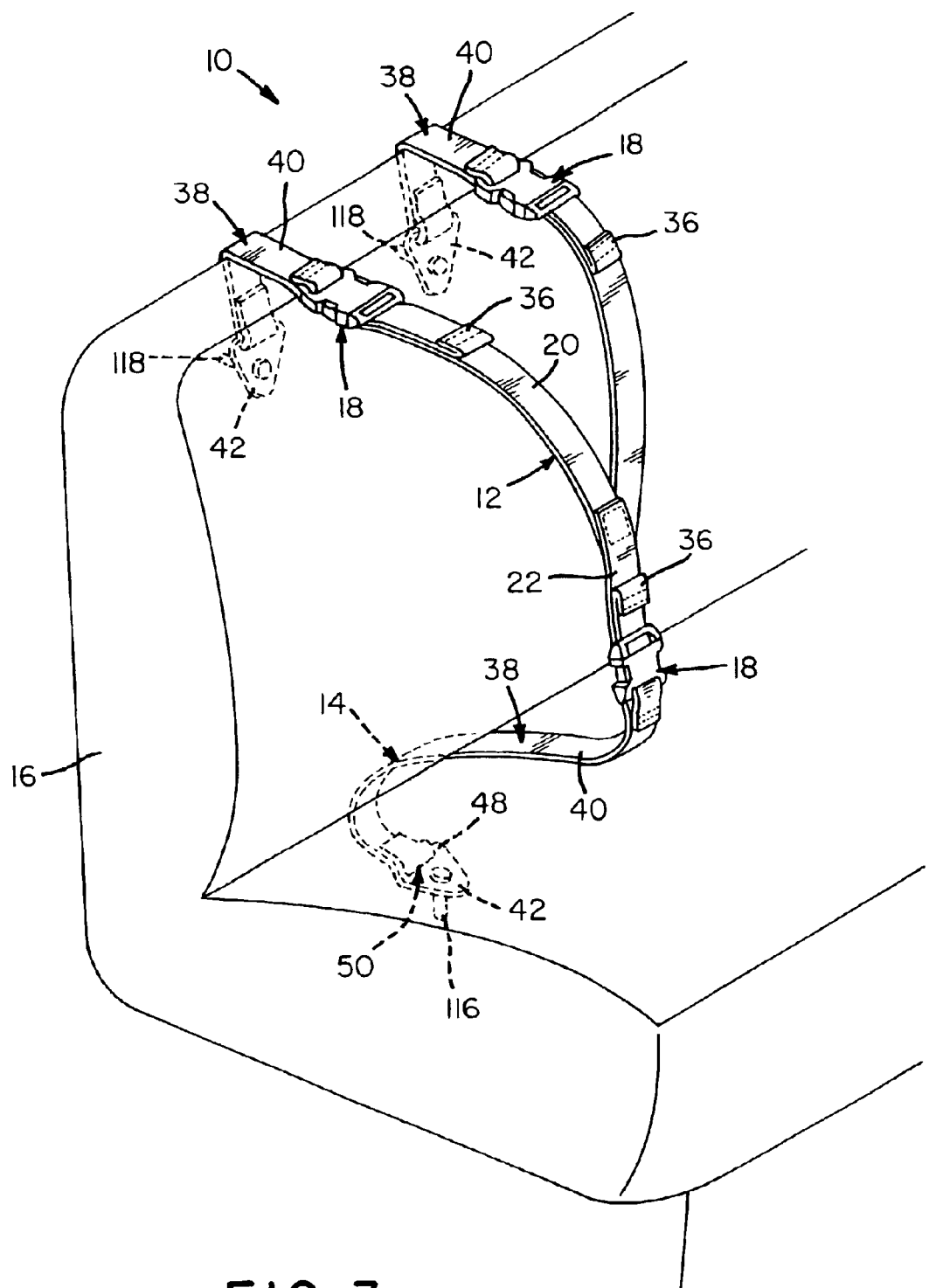
FIG. 3 is a perspective view of the restraining harness of FIG. 1 positioned adjacent a vehicle seat.

Referring now to the FIGS., a restraining harness in accordance with the present invention is shown at 10. Restraining harness 10 includes a torso binder 12 and an anchor assembly 14 for securing torso binder 12 adjacent a vehicle seat 16. A plurality of releasable fasteners 18 associated with torso binder 12 and anchor assembly 14 permit torso binder 12 to be rapidly attached and detached from seat 16 for ease in handling a handcuffed prisoner (not shown).

Torso binder 12 has a Y-shaped configuration for positioning over the shoulders and through the crotch of a prisoner being restrained thereby. This Y-shaped configuration is, preferably, obtained by sewing the bottoms of a pair of shoulder straps 20 to the top of crotch strap 22 such that shoulder straps 20 project upwardly and outwardly from crotch strap 22. To the free ends of straps 20 and 22 are secured the male components or portions 24 of releasable fasteners 18.

Each of the male components 24 includes a body 26 having an alignment arm 28, flanked by a pair or flexible gripping arms 30, extending from one of its ends. At the other end of body 26 is a slot 32 through which is run one of straps 20 or 22. A post 34 joins opposite ends of slot 32 together. Over post 34 a strap 20 or 22 is folded in a well-known manner so that the usable length thereof can be selectively varied. To prevent male components 24 from detaching from straps 20 and 22, the free ends of straps 20 and 22 are folded back upon themselves and sewn in place to form stops 36 incapable of passing through slots 32 and past posts 34.

Anchor assembly 14 includes a plurality of anchors 38. Each anchor 38 includes an anchor strap 40 with a mounting bracket 42 secured to one end thereof and a female component or portion 44 of a releasable fastener 18 secured to the other end thereof. Each mounting bracket 42 is a rigid plate having a hole 46 in its center and an upstanding tab 48 at one of its ends. Tab 48 is provided with a slot 50 through which one end of an anchor strap 40 can be passed, folded back upon itself and sewn so as to form a loop 52 for retaining mounting bracket 42. Each female component 44, however, includes a tubular body 54 having recesses 56 in its opposite sides open to its interior for releasably receiving the gripping arms 30 of a male component 24 inserted into the open end 58 of tubular body 44. A slot 60 is provided in the end of tubular body 54 opposite open end 58 through which the other end of an anchor strap 38 can be extended. A loop 62 formed by folding anchor strap 38 back upon itself and sewing in place retains female component 44 on anchor strap 38.

Figure 4:
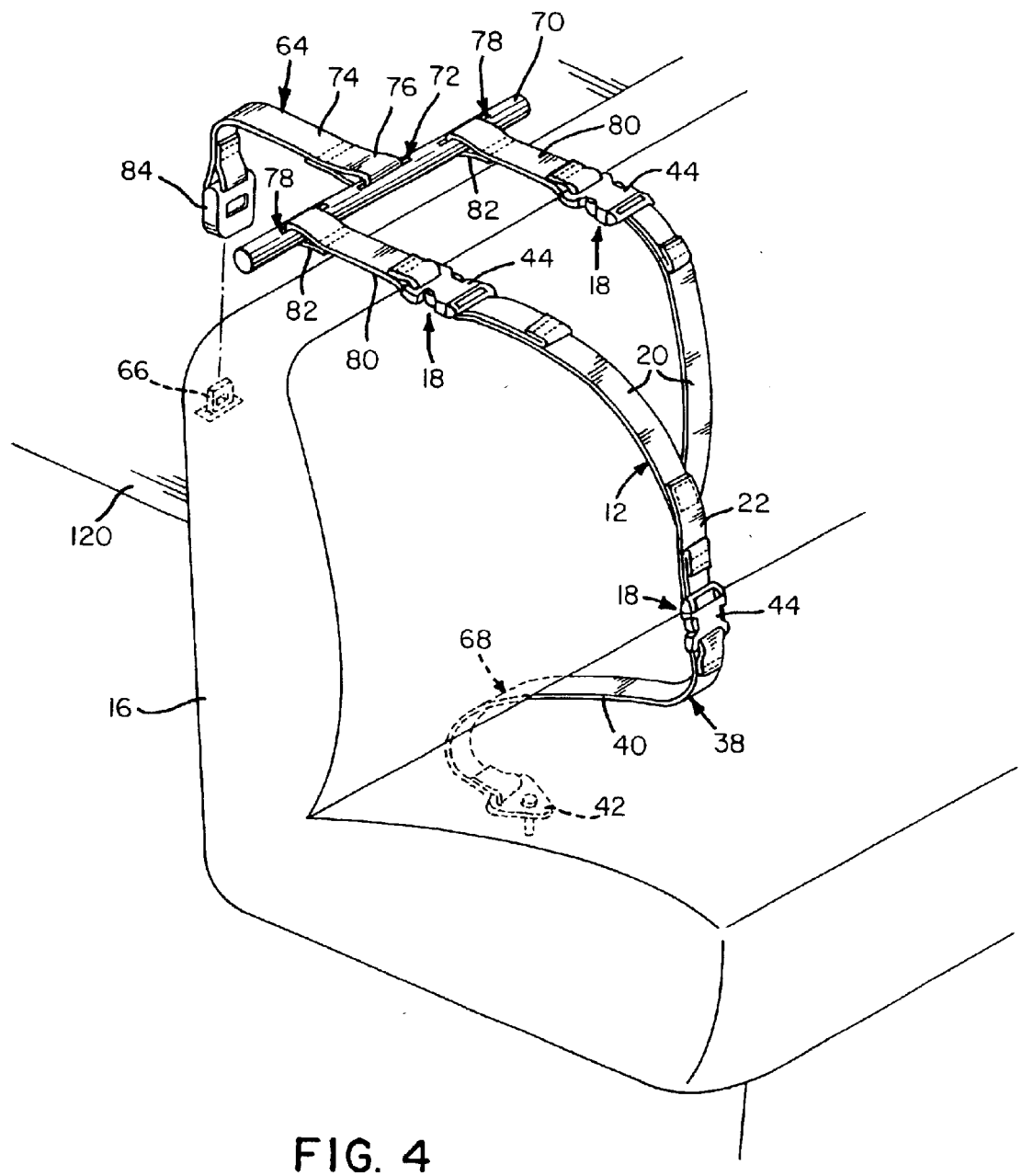
FIG. 4 is a perspective view of an alternative restraining harness in accordance with the invention positioned adjacent a vehicle seat.

Referring now to FIG. 4, a straddle mount 64 may be seen to provide an easy way to secure shoulder straps 20 of torso binder 12 adjacent to a prisoner's shoulders in vehicles equipped with a well-known, male-type children's car seat fastener 66. Straddle mount 64 forms a part of an anchor assembly 68 along with an anchor 38. Preferably, straddle mount 64 includes a rigid bar 70 having a slot 72 at its midpoint through which the bottom of an anchor strap 74 is extended. A loop 76 formed by folding anchor strap 74 back upon itself and sewing in place retains bar 70 on anchor strap 74. Likewise, bar 70 has a slot 78 at each of its ends through which the tops of a pair of anchor straps 80 are extended. Loops 82 formed by folding anchor straps 80 back upon themselves and sewing in place retain bar 70 on anchor straps 80.

Anchor straps 74 and 80 carry fastener components at their free ends, remote from bar 70. To the top of anchor strap 74 is secured a female component 84 of a releasable fastener of the type commonly employed in stabilizing children's car seats. The female component 44 of a releasable fastener 18 is secured to the free end of each anchor strap 40 and 80 for receiving the male component 24 of one correspondingly positioned releasable fastener 18 carried by torso binder 12.

Since the use of torso binder 12 in vehicles having bucket-style seats where mounting anchors 38 proximate the shoulders of a prisoner is difficult, if not impossible, another anchor assembly 88 has been developed. Anchor assembly 88 includes an endless band 90 for snugly encircling a vehicle seat 92. One anchor strap 94 is sewn at its top to band 90 and extends downwardly therefrom so that it can be passed underneath seat 92. A pair of flanking anchor straps 96 is sewn at their bottoms to band 90 and extend upwardly therefrom so that they can be passed over seat 92. The female component 44 of a releasable fastener 18 is secured to the free end of each anchor strap 94 and 96 for receiving the male component 24 of one correspondingly positioned releasable fastener 18 carried by torso binder 12.

Figure 5:
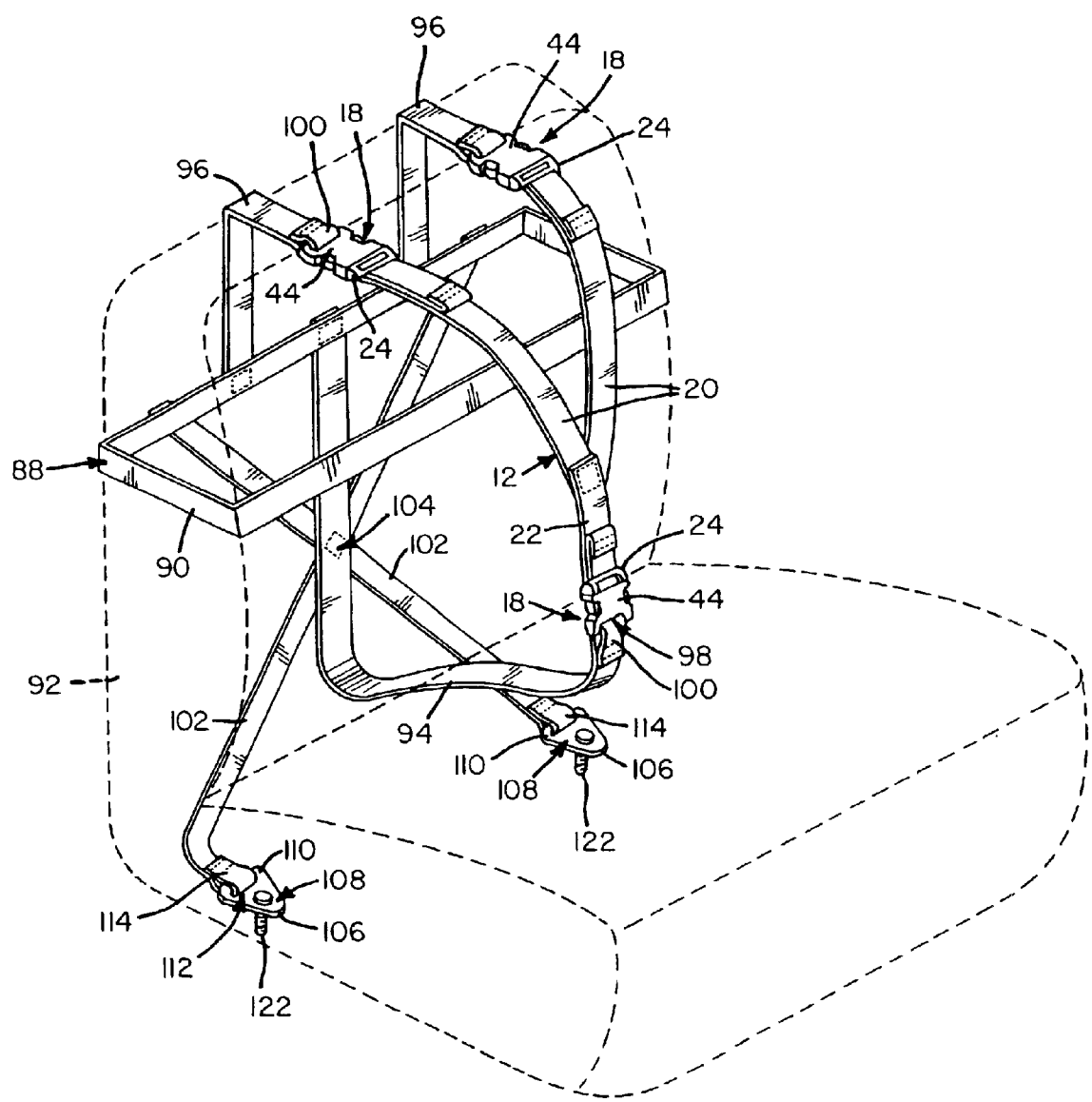
FIG. 5 is a perspective view of another alternative restraining harness in accordance with the present invention positioned adjacent a vehicle seat.

Each female component 44 of FIG. 5 is provided with a slot as at 98 through which an anchor strap 94 or 96 can be extended. A loop 100 formed by folding anchor strap 94 or 96 back upon itself and sewing in place retains each female component 44 on anchor strap 94 or 96.

A pair of tie-down straps 102 ensures that anchor assembly 88 cannot, under normal circumstances, be disengaged from seat 92. As shown, the top of each tie-down strap 102 is sewn to band 88 on opposite sides of anchor strap 94. Tie-down straps 102 extend downwardly from band 90 and crisscross one another substantially at right angles at a location 104 atop anchor strap 94. At location 104, straps 94 and 102 are sewn to one another.

The free ends of tie-down straps 102 extend below point 104 and carry mounting brackets 106. Mounting brackets 106 are like mounting brackets 42 and are a rigid plate with a hole 108 in its center and an upstanding tab 110 at one of its ends. Tab 110 is provided with a slot 112 through which the free end of a tie-down strap 102 is passed, folded back upon itself and sewn so as to form a loop 114 for retaining a mounting bracket 106.

Installation of restraining harness 10 in an automobile with a rear bench-type seat 16 is straightforward. First, the rear bench-type seat cushions are removed and a hole (not shown) is drilled in the floor of the vehicle midway between the attachment points for a selected pair of factory-installed seat belts (not shown). Then, a pair of holes (not shown) is drilled in the rear deck of the vehicle a few inches below the top of the seat 16 and a few inches to either side of an imaginary line extending upwardly through the seat 16 from the first-drilled hole. Next, a threaded fastener 116 is extended through hole 42 in mounting bracket 42 of anchor 38 for retaining crotch strap 22 and through the first-drilled hole to secure said anchor 38 to the vehicle. Similarly, a pair of threaded fasteners 118 is extended through the two holes in the seat deck and holes 46 in the mounting brackets 42 on anchors 38 for retaining shoulder straps 20. Finally, while making sure that anchor straps 38 remain fully accessible to people in the automobile, the rear seat cushions are reinstalled.

The optional straddle mount 64 can be used in place of two anchors 38 in automobiles having child seat anchors 66 incorporated into the rear deck 120. Here, anchor 38 is mounted as described in the previous paragraph. Next, female component 84 associated with straddle mount 64 is fastened in the usual manner to the male component 66 forming part of the vehicle. With anchor straps 80 extending from bar 70 downwardly over the top of the seat 16, restraining harness of FIG. 4 is ready to use.

The installation of the restraining harness need not be limited to vehicles with bench-type seats. By means of anchor assembly 88, torso binder 12 can be employed with bucket-type seats commonly found in the front of a vehicle. To employ anchor assembly 88, band 90 is slipped around seat 92 and moved downwardly until it cannot be moved further. Next, mounting brackets 106 at the bottoms of tie-down straps 102 are secured by means of threaded fasteners 122 extended through holes 108 to the floor of the vehicle adjacent the rear of the seat 92. Then, anchor strap 94 is pushed upwardly and forwardly between the seat cushion and backrest to emerge atop the seat cushion. Anchor straps 96 are, likewise, pushed upwardly and forwardly to rest atop the backrest. When a prisoner sits in seat 92, anchor strap 94 will project forwardly from a point beneath the prisoner's buttocks and to a location between his thighs, and anchor straps 96 will be positioned adjacent his shoulders.

All prisoners held by the restraining harness must be properly handcuffed with their hands behind their backs prior to entry into the restraining harness. Of course, handcuffing prevents the prisoner from reaching forward to release fasteners 18 so as to free himself. Equally important, handcuffing prevents the prisoner from attacking one having custody of the prisoner when placing him within the restraining harness or removing him from the restraining harness.

Once the prisoner is handcuffed and placed in a seat equipped with the restraining harness, torso binder 12 is secured about him. First, the male and female components 24 and 44 of releasable fasteners 18 are engaged with one another in a mated relationship. Next, the usable lengths of crotch and shoulder straps 20 and 22 are adjusted by pulling any excess lengths of straps 20 or 22 through slots 32 in male components 24. When finished, torso binder 12 should be snugly positioned against a prisoner with the intersection of crotch strap 22 and shoulder straps 20 falling upon the sternum of the prisoner. To the extent possible, the prisoner's back should rest flush with the backrest with only enough room for the prisoner's cuffed hands to rest comfortably. In normal use, the restraining harness should not cause any discomfort to the prisoner.

Once the prisoner has been secured by means of the restraining harness in a vehicle, the factory-installed seatbelts are positioned over the restraining harness to ensure the prisoner's safety while the vehicle is in motion. When the prisoner has reached a destination where his presence is required, his seat belt is disengaged and, then, torso binder 12 is disengaged by releasing the male and female components 24 and 44 of fasteners 18 from one another. Releasing the torso binder 12, like attaching such, requires only a few seconds to accomplish.

Using the restraining harness with anchor assemblies 68 and 88 is accomplished in substantially the same manner at that described above with anchor assembly 14. The only difference is that instead of coupling the male components 24 of releasable fasteners 18 on shoulder straps 20 to female components 44 carried by anchor straps 38, the male components 24 of shoulder straps 20 are coupled to the female components 44 of the straddle mount 64 or the male components 24 of straps 20 and 22 are coupled to the female components 44 of anchor assembly 88. The usable length of straps 20 and 22 is adjusted by pulling excess through slots 32 in male components 24.

When not in use, the restraining harness is easily stored in a compact manner. Torso binder 12, for example, can be wound into a ball the size of a fist and packed into a vehicle's glove compartment or trunk. Straddle mount 64, being equally small in size can be similarly located in an out of the way spot for reuse. Because anchors 38 and anchor assembly 88 are more permanently fastened to a vehicle, it is anticipated that they would be left in place after installation. Of course, the free ends of straps 40, 94 and 96 can be tucked into a seat so that they do not intrude upon other activities carried out in the vehicle. Thus, the restraining harness remains always ready for reuse on a moments notice.

While the restraining harness has been described with a high degree of particularity, it will be appreciated by those skilled in the art that modifications may be made thereto. For example, the restraining harness can employ buckles like those commonly used automobile and aircraft seat belts in place of releasable fasteners 18. (Of course, any suitable releasable fastener can be so used.) Furthermore, the endless band 90 forming part of anchor assembly 88 could be made adjustable in terms of length by providing a cut along its length wherein the resulting two adjacent ends can be releasably joined by suitable fasteners. Therefore, it is to be understood that the present invention is not limited to the several embodiments described above, but encompasses any and all embodiments within the scope of the following claims.

I claim:

1. A restraining harness, comprising:
    a torso binder having a pair of shoulder straps secured to a crotch strap so as to project upwardly and outwardly therefrom, each of said shoulder and crotch straps having a first releasable fastener portion secured thereto; and,
    an anchor assembly for selectively securing said torso binder adjacent a seat, said anchor assembly having a plurality of second releasable fastener portions each being adapted for selective mated engagement with one said first releasable fastener portion.

2. The restraining harness according to claim 1 wherein said anchor assembly further comprises a plurality of anchors, each of which including an anchor strap with a mounting bracket secured to one end thereof and one of said second releasable fastener portions secured to the other end thereof.

3. The restraining harness according to claim 1 wherein said anchor assembly further comprises a straddle mount including:
    a rigid bar having opposed ends and a midpoint between said opposed ends;
    a first anchor strap being secured at its bottom to said midpoint of said bar;
    a pair of second anchor straps, each being secured at its top to a respective one of said opposed ends of said bar;
    a pair of second releasable fastener portions each being secured to a respective one of said second anchor straps and each being adapted for selective mated engagement with a respective one of said first releasable fastener portions carried by said shoulder straps; and,
    a third releasable fastener portion being secured to said first anchor strap for selective mated engagement with a car seat fastener of a land vehicle.

4. The restraining harness according to claim 1 wherein said anchor assembly further comprises:
    a band for encircling a seat;
    a first anchor strap being secured to said band and extending downwardly therefrom so that such can be passed underneath the seat
    a pair of second anchor straps being secured to said band and extending upwardly therefrom so that such can be passed over the seat
    a plurality of second releasable fastener portions each being secured to a respective one of said first and second anchor straps.

5. The restraining harness according to claim 4 wherein said anchor assembly further includes a pair of tie-down straps being secured to said band on opposite sides of said first anchor strap and extending downwardly from said band, each of said tie-down straps carrying a mounting bracket for attachment to a surface supporting the seat.

6. A restraining harness, comprising:
    a torso binder having a pair of shoulder straps secured to a crotch strap so as to project upwardly and outwardly from said crotch strap, each of said shoulder and crotch straps having a first releasable fastener portion slidably secured thereto; and, an anchor assembly for selectively securing said torso binder adjacent a seat, said anchor assembly having a plurality of second releasable fastener portions each being adapted for selective mated engagement with one said first releasable fastener portion.

7. The restraining harness according to claim 6 wherein said anchor assembly further comprises a plurality of anchors, each of which including an anchor strap with a mounting bracket secured to one end thereof for securing said anchor strap to a support for the seat and one of said second releasable fastener portions secured to the other end thereof.

8. The restraining harness according to claim 6 wherein said anchor assembly further comprises:
- a straddle mount including:
  - a rigid bar having first opposed ends and a midpoint between said first opposed ends;
  - a first anchor strap being secured at its bottom to said midpoint of said bar;
  - a pair of second anchor straps, each being secured at its top to a respective one of said first opposed ends of said bar;
  - a pair of second releasable fastener portions each being secured to a respective one of said second anchor straps and each being adapted for selective mated engagement with a respective one of said first releasable fastener portions carried by said shoulder straps; and,
  - a third releasable fastener portion being secured to said first anchor strap for selective mated engagement with a car seat fastener of a land vehicle; and,
- an anchor including:
  - an anchor strap having second opposed ends:
    - a mounting bracket being secured to one of said second opposed ends for attachment to the support for a seat; and,
    - one of said second releasable fastener portions being secured to the other one of said second opposed ends and being adapted for selective mated engagement with a said first releasable fastener portions secured to said crotch strap.

9. A restraining harness, comprising:
- a torso binder having a pair of shoulder straps secured to a crotch strap so as to project upwardly and outwardly therefrom, each of said shoulder and crotch straps having a first releasable fastener portion secured thereto; and,
- an anchor assembly for selectively securing said torso binder adjacent a seat, said anchor assembly, said anchor assembly including:
  - a band for encircling a seat;
  - a first anchor strap being secured to said band and extending downwardly therefrom so that such can be passed underneath the seat
  - a pair of second anchor straps being secured to said band and extending upwardly therefrom so that such can be passed over the seat
  - a plurality of second releasable fastener portions each being secured to a respective one of said first and second anchor straps second releasable fastener portions, each of said second releasable fastener portions being adapted for selective mated engagement with a respective one of said first releasable fastener portions.

* * * * *